(12) United States Patent
Sasaki et al.

(10) Patent No.: US 11,482,318 B2
(45) Date of Patent: Oct. 25, 2022

(54) MEDICAL INFORMATION PROCESSING SYSTEM

(71) Applicant: OLYMPUS CORPORATION, Tokyo (JP)

(72) Inventors: Akinori Sasaki, Tokyo (JP); Yoshiko Ikeda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 481 days.

(21) Appl. No.: 16/720,224

(22) Filed: Dec. 19, 2019

(65) Prior Publication Data
US 2020/0126655 A1 Apr. 23, 2020

Related U.S. Application Data

(63) Continuation of application No. PCT/JP2018/016156, filed on Apr. 19, 2018.

(30) Foreign Application Priority Data

Jun. 19, 2017 (JP) .............................. JP2017-119817

(51) Int. Cl.
*G16H 30/20* (2018.01)
*G10L 25/03* (2013.01)
(Continued)

(52) U.S. Cl.
CPC ........... *G16H 30/20* (2018.01); *A61B 1/0005* (2013.01); *A61B 1/00009* (2013.01);
(Continued)

(58) Field of Classification Search
CPC .. G16H 30/20; A61B 1/00009; A61B 1/0005; A61B 1/043; A61B 1/0661; G10L 15/26; G10L 25/03
See application file for complete search history.

(56) References Cited

U.S. PATENT DOCUMENTS

2008/0097155 A1* 4/2008 Gattani .............. A61B 1/00042
600/117
2010/0086286 A1* 4/2010 Lee ........................ A61B 1/041
600/109

FOREIGN PATENT DOCUMENTS

JP 2006-015125 A 1/2006
JP 2012-065735 A 4/2012
(Continued)

OTHER PUBLICATIONS

Japanese Office Action dated Feb. 2, 2021 received in 2019-525165.
(Continued)

*Primary Examiner* — Thai Q Tran
*Assistant Examiner* — Jose M Mesa
(74) *Attorney, Agent, or Firm* — Scully, Scott, Murphy & Presser, P.C.

(57) ABSTRACT

An examination image storage stores a plurality of examination images having image-capturing time information. A voice processing unit extracts information regarding a finding by recognizing voice that is input to a microphone, and an extracted information storage stores the extracted information regarding the finding and voice time information in association with each other. A grouping processing unit groups a plurality of examination images into one or more image groups based on the image-capturing time information. An association processing unit associates the information regarding the finding stored in the extracted information storage with an image group based on the voice time information. When one examination image is selected by a user, a finding selection screen generation unit generates a screen that displays information regarding a finding associated with an image group including the examination image that is selected.

11 Claims, 11 Drawing Sheets

(51) Int. Cl.
    *G10L 15/26*    (2006.01)
    *A61B 1/00*     (2006.01)
    *A61B 1/04*     (2006.01)
    *A61B 1/06*     (2006.01)

(52) U.S. Cl.
    CPC ............ *A61B 1/043* (2013.01); *A61B 1/0661* (2013.01); *G10L 15/26* (2013.01); *G10L 25/03* (2013.01)

(56) References Cited

FOREIGN PATENT DOCUMENTS

| | | | |
|---|---|---|---|
| JP | 2012-070839 A | 4/2012 | |
| JP | 2013-048990 A | 3/2013 | |
| JP | 2016-054775 A | 4/2016 | |
| JP | 2016-085505 A | 5/2016 | |
| JP | 2016-123719 A | 7/2016 | |
| WO | WO-2010120061 A2 * | 10/2010 | ......... A61B 1/00009 |
| WO | WO-2011121986 A1 * | 10/2011 | ......... A61B 1/00009 |

OTHER PUBLICATIONS

International Search Report dated Jul. 10, 2018 issued in International Application No. PCT/JP2018/016156.
International Preliminary Report on Patentability dated Dec. 24, 2019, together with the Written Opinion received in related International Application No. PCT/JP2018/016156.

\* cited by examiner

FIG.2

| VOICE DATA NUMBER | VOICE TIME | VOICE CONTENT | EXTRACTED FINDING |
|---|---|---|---|
| 1 | 0:36 | THERE IS NO ABNORMALITY. | NO ABNORMALITY |
| 2 | 1:20 | NO ABNORMALITY FOUND. | NO ABNORMALITY |
| 3 | 2:05 | NO PROBLEM. | NO ABNORMALITY |
| 4 | 4:08 | THIS IS A TUMOR. 2cm. | TUMOR, 2cm |
| 5 | 4:45 | LARGE | LARGE |
| 6 | 5:11 | POSSIBLE EARLY GASTRIC CANCER | EARLY GASTRIC CANCER SUSPECTED |
| 7 | 8:01 | NO ABNORMALITY FOUND. | NO ABNORMALITY |
| 8 | 9:13 | THERE IS NO ABNORMALITY. | NO ABNORMALITY |

| IMAGE NUMBER | IMAGE-CAPTURING TIME | OBSERVATION MODE |
|---|---|---|
| 1 (104a) | 0:15 | NORMAL LIGHT OBSERVATION |
| 2 (104b) | 0:43 | NORMAL LIGHT OBSERVATION |
| 3 (104c) | 0:55 | NORMAL LIGHT OBSERVATION |
| 4 (104d) | 2:21 | NORMAL LIGHT OBSERVATION |
| 5 (104e) | 3:40 | NORMAL LIGHT OBSERVATION |
| 6 (104f) | 3:45 | NARROWBAND LIGHT OBSERVATION |
| 7 (104g) | 3:51 | NARROWBAND LIGHT OBSERVATION |
| 8 (104h) | 4:06 | NARROWBAND LIGHT OBSERVATION |
| 9 (104i) | 4:25 | NARROWBAND LIGHT OBSERVATION |
| 10 (104j) | 4:50 | NARROWBAND LIGHT OBSERVATION |
| 11 (104k) | 5:10 | NARROWBAND LIGHT OBSERVATION |
| 12 (104l) | 5:23 | NARROWBAND LIGHT OBSERVATION |
| 13 (104m) | 5:51 | NARROWBAND LIGHT OBSERVATION |
| 14 (104n) | 7:12 | NORMAL LIGHT OBSERVATION |
| 15 (104o) | 7:45 | NORMAL LIGHT OBSERVATION |
| 16 (104p) | 8:13 | NORMAL LIGHT OBSERVATION |
| 17 (104q) | 8:45 | NORMAL LIGHT OBSERVATION |
| 18 (104r) | 9:00 | NORMAL LIGHT OBSERVATION |
| 19 (104s) | 9:12 | NORMAL LIGHT OBSERVATION |
| 20 (104t) | 9:19 | NORMAL LIGHT OBSERVATION |
| 21 (104u) | 9:25 | NORMAL LIGHT OBSERVATION |

FIG.5

| IMAGE NUMBER | IMAGE-CAPTURING TIME | OBSERVATION MODE | IMAGE GROUP |
|---|---|---|---|
| 1 (104a) | 0:15 | NORMAL LIGHT OBSERVATION | GROUP 1 |
| 2 (104b) | 0:43 | NORMAL LIGHT OBSERVATION | GROUP 1 |
| 3 (104c) | 0:55 | NORMAL LIGHT OBSERVATION | GROUP 1 |
| 4 (104d) | 2:21 | NORMAL LIGHT OBSERVATION | GROUP 1 |
| 5 (104e) | 3:40 | NORMAL LIGHT OBSERVATION | GROUP 1 |
| 6 (104f) | 3:45 | NARROWBAND LIGHT OBSERVATION | GROUP 2 |
| 7 (104g) | 3:51 | NARROWBAND LIGHT OBSERVATION | GROUP 2 |
| 8 (104h) | 4:06 | NARROWBAND LIGHT OBSERVATION | GROUP 2 |
| 9 (104i) | 4:25 | NARROWBAND LIGHT OBSERVATION | GROUP 2 |
| 10 (104j) | 4:50 | NARROWBAND LIGHT OBSERVATION | GROUP 2 |
| 11 (104k) | 5:10 | NARROWBAND LIGHT OBSERVATION | GROUP 2 |
| 12 (104l) | 5:23 | NARROWBAND LIGHT OBSERVATION | GROUP 2 |
| 13 (104m) | 5:51 | NARROWBAND LIGHT OBSERVATION | GROUP 2 |
| 14 (104n) | 7:12 | NORMAL LIGHT OBSERVATION | GROUP 3 |
| 15 (104o) | 7:45 | NORMAL LIGHT OBSERVATION | GROUP 3 |
| 16 (104p) | 8:13 | NORMAL LIGHT OBSERVATION | GROUP 3 |
| 17 (104q) | 8:45 | NORMAL LIGHT OBSERVATION | GROUP 3 |
| 18 (104r) | 9:00 | NORMAL LIGHT OBSERVATION | GROUP 3 |
| 19 (104s) | 9:12 | NORMAL LIGHT OBSERVATION | GROUP 3 |
| 20 (104t) | 9:19 | NORMAL LIGHT OBSERVATION | GROUP 3 |
| 21 (104u) | 9:25 | NORMAL LIGHT OBSERVATION | GROUP 3 |

CAPTURED IMAGE. REPORT

PATIENT NAME:PATIENT A DATE OF BIRTH:1981/11/19 EXAMINATION TYPE:UPPER ENDOSCOPIC PERFORMING DOCTOR:DOCTOR B
EXAMINATION
PATIENT ID: 123456 EXAMINATION DATE: 2017/5/15

100a — RECORDED IMAGE
100b — REPORT
100c — IMAGE GROUP

102 →

☑ INCLUDE PATHOLOGICAL ORDERS

OBSERVATION RANGE [EDIT] — 108 ESOPHAGUS, STOMACH, DUODENUM — 110

ESOPHAGUS
STOMACH
DUODENUM 104a  104b  104c
104d  104e  104f
104g  104h  104i
104j  104k  104l

ATTACHMENT TO REPORT (ESOPHAGUS)
ATTACHMENT TO REPORT (STOMACH)
ATTACHMENT TO REPORT (DUODENUM)
— 112

114 —
HIS ANGLE
CARDIAC REGION
ANGULAR REGION
GASTRIC BODY
GASTRIC FUNDUS
FORNIX
PYLORIC ZONE
PYLORUS

[REGISTER] [SAVE TEMPORARILY] [CLOSE]

CAPTURED IMAGE, REPORT

PATIENT NAME: PATIENT A   DATE OF BIRTH: 1981/11/19   EXAMINATION TYPE: UPPER ENDOSCOPIC   PERFORMING DOCTOR: DOCTOR B
PATIENT ID: 123456                                    EXAMINATION
                                                      EXAMINATION DATE: 2017/5/15

| RECORDED IMAGE | REPORT | IMAGE GROUP |

☑ INCLUDE PATHOLOGICAL ORDERS

OBSERVATION RANGE [EDIT]   ESOPHAGUS, STOMACH, DUODENUM

ESOPHAGUS   ☐ ~104a   ☐ ~104c
            NO ABNORMALITY

STOMACH     ☐ ~104h   ☐ ~104n   ☐ ~104q
            PART: GASTRIC FUNDUS     TUMOR: 2cm
            QUALITATIVE DIAGNOSIS: EARLY GASTRIC CANCER SUSPECTED
            VISIBLE TYPE: 0-I (PROTRUDING TYPE)

DUODENUM    ☐ ~104t
            NO ABNORMALITY

~104j   ~104k   ~104i
~104m   ~104n   ~104o
~104p   ~104q   ~104r
~104s   ~104t   ~104u

[REGISTER] [SAVE TEMPORARILY] [CLOSE]

80   90

MEDICAL INFORMATION PROCESSING SYSTEM

CROSS-REFERENCE TO RELATED APPLICATIONS

This application is based upon and claims the benefit of priority from the prior Japanese Patent Applications No. 2017-119817, filed on Jun. 19, 2017, and International Application No. PCT/JP2018/016156, filed on Apr. 19, 2018, the entire contents of which are incorporated herein by reference.

BACKGROUND OF THE INVENTION

1. Field of the Invention

The present invention relates to a medical information processing system that effectively uses voice uttered by a doctor and the like during an examination.

2. Description of the Related Art

Patent Document 1 discloses a medical image processing device including: a display control means that displays a medical image or a monitor image stored in a storage medium on a display device; and a voice reproduction control means that causes a voice reproduction device to reproduce voice stored in the storage medium in association with the medical image or the monitor image displayed on the display device.

[Patent Document 1] Japanese Patent Application Publication No. 2013-48990

In an endoscopic examination, a doctor inserts an endoscope into a patient's body and displays patient's internal body images on a display device in real time. When the doctor observes an image displayed on the display device and finds an area of concern such as a pathological change or bleeding, the doctor operates a release switch of the endoscope so as to capture a still image of the internal body. After the examination is completed, the doctor enters a diagnosis detail including finding information on a report input screen, attaches necessary examination images, and creates an examination report. Doctors rely on memory to enter diagnosis. However, if a mechanism is built that assists the work of entering diagnosis, it is expected that the workload of the doctors will be reduced and errors such as missed entry will be reduced as well.

SUMMARY OF THE INVENTION

In this background, a purpose of the present invention is to provide a technology necessary for assisting the work of entering reports and the like performed by doctors.

A medical information processing system according to an embodiment of the present invention includes: an examination image storage that stores a plurality of examination images having image-capturing time information indicating image-capturing time; a voice processing unit that extracts information regarding a finding based on voice that is input to a voice input unit; an extracted information storage that stores information regarding the finding that is extracted and voice time information indicating the time the voice is input to the voice input unit in association with each other; a grouping processing unit that groups the plurality of examination images into one or more image groups based on the image-capturing time information; and an association processing unit that associates the information regarding the finding stored in the extracted information storage with the image group based on the voice time information.

Optional combinations of the aforementioned constituting elements and implementations of the invention in the form of methods, apparatuses, systems, recording mediums, and computer programs may also be practiced as additional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 2 is a diagram illustrating an example of information regarding findings stored in an extracted information storage;

FIG. 4 is a diagram illustrating an example of metadata of an examination image;

FIG. 5 is a diagram illustrating the result of grouping by a grouping processing unit;

FIG. 6 is a diagram illustrating an example of a presentation screen for image groups that have been grouped;

FIG. 7 is a diagram illustrating the state of association by an association processing unit;

FIG. 8 is a diagram illustrating an example of a menu window for selecting an image to be attached to a report;

FIG. 11 is a diagram illustrating examination results including diagnosis entered on the report entry screen.

DETAILED DESCRIPTION OF THE INVENTION

The invention will now be described by reference to the preferred embodiments. This does not intend to limit the scope of the present invention, but to exemplify the invention.

Figure 1:
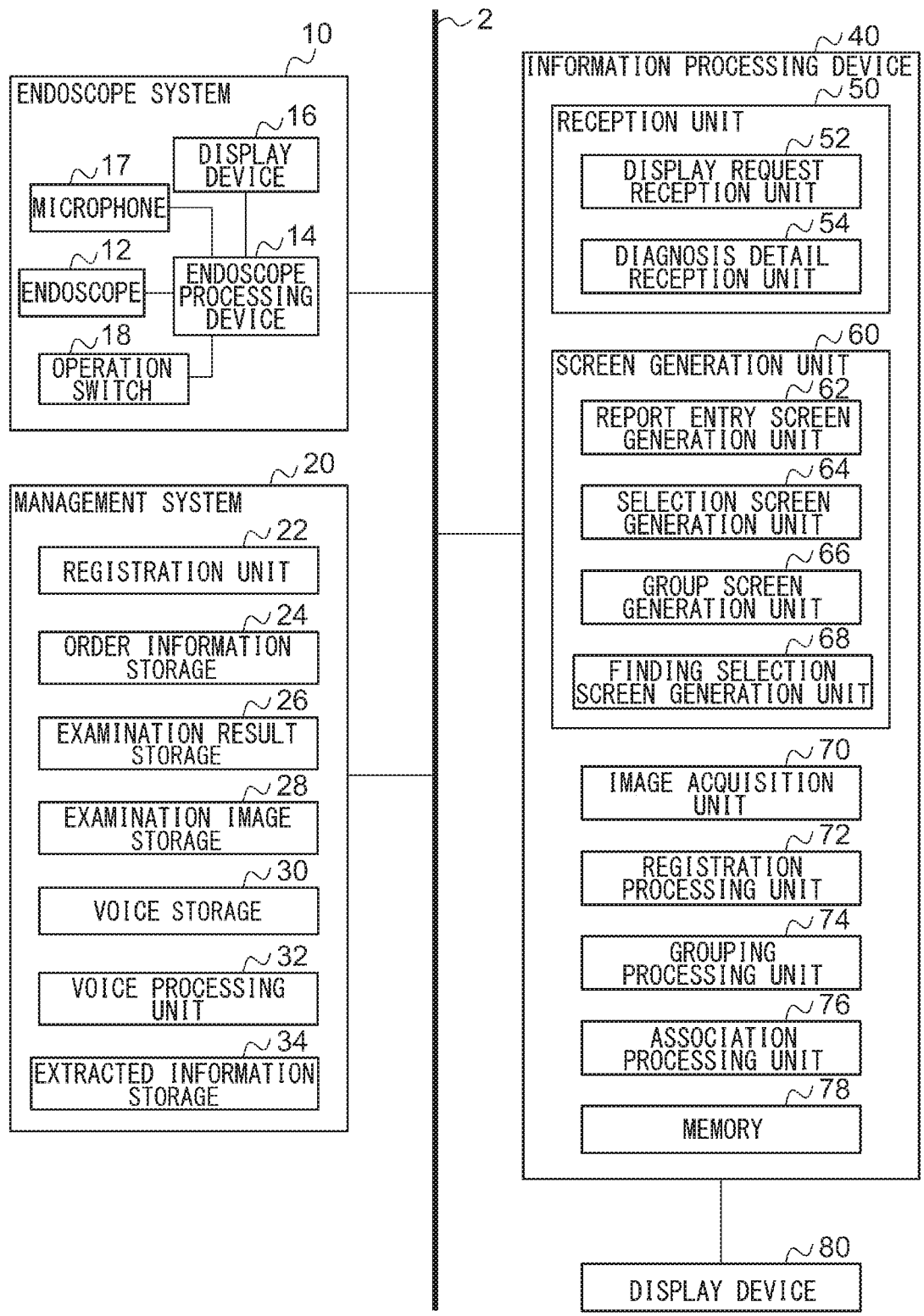
FIG. 1 is a diagram illustrating the configuration of a medical information processing system according to an embodiment.

FIG. 1 illustrates the configuration of a medical information processing system 1 according to an embodiment of the present invention. The medical information processing system 1 according to an embodiment is a system for assisting an endoscopic examination report preparation task in a medical facility. The medical information processing system 1 includes an endoscope system 10, a management system 20, and an information processing device 40, which are interconnected by a network 2 such as a LAN (local area network). The information processing device 40 is a terminal device such as a personal computer and is connected to a display device 80 such that output can be displayed on the screen. The information processing device 40 may be a laptop computer integrated with a display device or a portable tablet. Further, the information processing device 40 may be comprised of a combination of a terminal device and a server.

The endoscope system 10 is provided in an endoscopic examination room and includes an endoscope 12, an endoscope processing device 14, a display device 16, a microphone 17, and an operation switch 18. The endoscope 12 is inserted into the patient's body, and a still image of the inside of the body is captured at the timing when the doctor presses a release switch of the endoscope 12. The endoscope 12 is provided with a solid-state imaging device (for example, CCD image sensor or CMOS image sensor) and a signal processing circuit. The solid-state imaging device converts incident light into an electrical signal, and the signal processing circuit performs signal processing such as A/D conversion, noise removal, and the like on image data photoelectric-converted by the solid-state imaging device and outputs the resulting image data to the endoscope processing device 14.

The endoscope 12 according to the embodiment has a special light observation function for NBI (narrowband light observation), AFI (fluorescence observation), and IRI (infrared light observation) in addition to a normal light observation function using white light as the type of observation mode for an endoscopic examination. These observation modes are set by pressing a function button provided on the endoscope 12. In each observation mode, the wavelength and intensity of irradiation light into the body are different. Therefore, an examination image captured in each observation mode has a different tone of color due to the difference in irradiation light.

The endoscope processing device 14 controls the entire endoscope system 10 in an integrated manner. One important role of the endoscope processing device 14 is to transmit an examination image captured by the endoscope 12 to the management system 20 and store the examination image in an examination image storage 28. Another important role is to display video acquired by the endoscope 12 on the display device 16 in real time.

In the former role, when the release switch of the endoscope 12 is pressed, the endoscope processing device 14 adds information identifying the examination (examination ID), information specifying the observation mode of the endoscopic examination (observation mode information), and image-capturing time information indicating the image-capturing time to the captured image of the endoscope 12 at least as metadata so as to generate examination image data. The endoscope processing device 14 transmits the examination image data to the examination image storage 28 of the management system 20, and the examination image storage 28 stores the examination image data.

In the medical information processing system 1 according to the embodiment, a mechanism is constructed such that utterance content uttered by the doctor during an examination can be used as finding information when an examination report is created later. When the doctor finds an area of concern such as a pathological change or bleeding while observing an internal body image displayed on the display device 16, the doctor presses the release switch so as to capture a still image. It is a common practice for doctors to capture a plurality of images particularly for a lesion site in order to observe again when creating an examination report. By capturing a plurality of images of a single lesion area in advance, the clearest lesion image can be selected when attaching an examination image to a report.

The doctor utters the content of a finding when observing an internal body image and causes the management system 20 to store the utterance content. The microphone 17 is a voice input unit that inputs voice and converts the voice into an electrical signal. The endoscope processing device 14 transmits voice data that is input to the microphone 17 to a voice storage 30 of the management system 20 along with voice time information indicating the time the voice is input to the microphone 17. The voice storage 30 stores the voice data and the voice time information in association with each other.

The microphone 17 may be in a power-on state during the time from the start of the examination to the end of the examination and may acquire all the voice during the examination. In this case, since all the voice data that is input to the microphone 17 during the examination is stored in the voice storage 30 in association with voice time information, utterance content other than finding information is also stored in the voice storage 30 as a result.

Therefore, the microphone 17 is preferably controlled to be turned on or off in accordance with a doctor's instruction. That is, the microphone 17 may be turned on only when the doctor wants to register finding information through voice. The operation switch 18 is a switch for instructing on/off of the microphone 17, and the doctor operates the operation switch 18 when he/she wants to utter and record a finding detail. In the embodiment, the operation switch 18 is a foot pedal switch arranged at a doctor's foot, and the doctor turns on the microphone 17 by stepping on the operation switch 18 with his/her foot immediately before uttering the finding details, and after uttering the finding details, the foot is removed from the operation switch 18, and the power of the microphone 17 is turned off. Compared to a case where the microphone 17 is always turned on, there is an advantage that the volume of the voice data can be reduced and the time required for the subsequent voice recognition process and the like can be reduced by recording only voice that is necessary. In the following embodiment, a case will be described in which a doctor registers finding information through voice while instructing the microphone 17 to be turned on/off through the operation switch 18.

The management system 20 includes a registration unit 22, an order information storage 24, an examination result storage 26, an examination image storage 28, a voice storage 30, a voice processing unit 32, and an extracted information storage 34. The order information storage 24 stores order information for an endoscopic examination. The examination result storage 26 stores the examination result of the endoscopic examination and specifically stores report information created by the information processing device 40 in association with examination information such as patient information and examination type information. The report information includes a diagnosis result such as diagnosis details entered by a doctor, a report attachment image selected from examination images that have been captured, a comment regarding the report attachment image, and the like.

The examination image storage 28 stores an examination image captured by the endoscope system 10. The examination image includes an examination ID, observation mode information, and image-capturing time information as metadata. The examination image storage 28 may be comprised of a large hard disk drive (HDD) or a flash memory.

In association with an examination ID, the voice storage 30 stores voice uttered by the doctor and input to the microphone 17 during the examination in association with voice time information indicating the time the voice is input to the microphone 17. The voice processing unit 32 performs voice recognition on the voice stored in the voice storage 30, converts the voice into a character string, performs language analysis on the character string as converted, and extracts at least information regarding a finding. The process performed by the voice processing unit 32 is performed after the examination is completed. The extracted information storage 34 stores the extracted information regarding the finding and the voice time information in association with each other.

For example, the voice processing unit 32 may perform a process of performing voice recognition on the voice stored in the voice storage 30, converting the voice into a character string, performing language analysis on the character string as converted, and extracting information regarding the finding at the timing when the examination is completed. At another timing, when the doctor selects an examination for generating an examination report from a list of performed examinations described later, the voice processing unit 32 may specify voice stored in the voice storage 30 based on the examination ID of the examination and perform a process of extracting information regarding a finding. As described above, the voice processing unit 32 may perform a voice recognition process and a language analysis process at an arbitrary timing after the completion of an examination. The voice processing unit 32 may perform voice recognition in real time. In that case, the voice processing unit 32 may temporarily store voice that is input to the microphone 17 in a buffer, perform voice recognition on the temporarily stored voice substantially in real time, and perform language analysis on a character string that has been identified.

FIG. 2 is shows an example of information regarding findings (extracted findings) stored in the extracted information storage 34. In this example, during the examination, the doctor operates the operation switch 18 eight times and inputs utterance content to the microphone 17 eight times. Accordingly, the voice storage 30 stores eight pieces of voice data related to this examination in association with respective pieces of voice time information. In FIG. 2, "voice time" indicates an elapsed time from the examination start time, and a voice data number is assigned to each piece of voice data in the order of input to the microphone 17.

The voice processing unit 32 performs a voice recognition process of voice data and converts the voice data into a character string. "Voice content" shown in FIG. 2 represents a character string extracted through voice recognition performed on voice data by the voice processing unit 32, that is, utterance content of the doctor. Since the voice content is a material for deriving information regarding a finding, the voice content may not be stored in the extracted information storage 34. However, FIG. 2 shows a state where the voice content is stored in the extracted information storage 34.

The voice processing unit 32 extracts information regarding a finding from the extracted character string. "Extracted finding" indicates information regarding a finding extracted from the character string. The information regarding a finding is preferably extracted such that the information can be entered as finding information on the report entry screen.

For example, in the report entry screen, when a plurality of finding items are displayed as selections and a format is formed in which finding information is entered by a doctor selecting a check box, the voice processing unit 32 preferably extracts information regarding a finding as a finding item. In other words, the voice processing unit 32 preferably extracts information regarding a finding from the character string that is the voice content such that the information can be directly used as a finding entry on the report input screen.

For example, if there is no abnormal finding, the doctor selects the check box of a "no abnormality" item on the report entry screen and performs a report entry. In the example shown in FIG. 2, voice data indicating that there is no abnormal finding is voice data having data numbers 1 to 3, 7, and 8. Therefore, the voice processing unit 32 extracts "no abnormality" as an extracted finding for each voice content item having voice data numbers 1 to 3, 7, and 8.

The voice processing unit 32 extracts finding information indicating "tumor, 2 cm" from voice content of the voice data number 4 stating "This is a tumor. 2 cm.". This is because an item stating "tumor, 2 cm" is set in the report entry screen. In addition, the voice processing unit 32 extracts diagnostic information indicating "early gastric cancer suspected" with respect to voice content of a voice data number 6 stating "possible early gastric cancer". This is also because an item stating ""early gastric cancer suspected" is set for an selection for a diagnosis detail in the report entry screen.

On the other hand, since the voice processing unit 32 cannot extract a corresponding report entry screen item for voice content having a voice data number 5 stating "large", the voice processing unit 32 does not change the voice content and sets "large" as an extracted finding. As described above, the voice processing unit 32 extracts finding information from the voice of the doctor before generating a report prepared by the doctor and stores the finding information in the extracted information storage 34 in association with voice time information.

Referring back to FIG. 1, the information processing device 40 has a function of assisting report preparation performed by a doctor in cooperation with the management system 20. A user interface such as a keyboard and a mouse is connected to the information processing device 40. The information processing device 40 causes the display device 80 to display a screen regarding an examination image and report preparation, and the doctor operates the user interface while looking at the display screen so as to finish the report.

The information processing device 40 accesses the management system 20 so as to display an examination image stored in the examination image storage 28 on the display device 80. When a doctor prepares an endoscopic examination report, thumbnails of all examination images linked to an examination ID and stored in the examination image storage 28 are read out by the information processing device 40, and a thumbnail list is displayed on the display device 80 such that the doctor can select an examination image to be attached to the report.

The information processing device 40 includes a reception unit 50, a screen generation unit 60, an image acquisition unit 70, a registration processing unit 72, a grouping processing unit 74, an association processing unit 76, and a memory 78. The reception unit 50 receives a user interface operation entry by a doctor, for example, a mouse and keyboard operation entry and has a display request reception unit 52 and a diagnosis detail reception unit 54. The screen generation unit 60 generates a screen to be displayed on the display device 80.

The configuration thereof is implemented by hardware such as a processor, a memory, or other LSIs and by software such as a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both. Further, as described above, although the information processing device 40 may be a terminal device, the information processing device 40 may be formed by a combination of a terminal device and a server. Therefore, each function shown as a component of the information processing device 40 in FIG. 1 may be realized by a device other than a terminal device.

After the completion of an endoscopic examination, the doctor enters a user ID and a password to the information processing device 40 so as to log in. When the doctor logs in, an application for preparing an examination report is automatically started, and a list of already performed examinations is displayed on the display device 80. The list of already performed examinations displays examination information such as the patient name, the patient ID, the examination date and time, the examination type, and the like in a list, and the doctor selects an examination for which a report is to be prepared. When a doctor selects an examination for which an examination report is to be prepared from a list of examinations that have been performed by a doctor, the display request reception unit 52 receives a report entry screen display request, and the image acquisition unit 70 acquires a thumbnail of an examination image linked to the examination ID of the examination that is selected from the examination image storage 28.

The screen generation unit 60 of the embodiment includes a report entry screen generation unit 62 for generating a report entry screen for entering a diagnosis detail, a selection screen generation unit 64 for generating a list screen of examination images captured in an examination, a group screen generation unit 66 for generating a presentation screen of examination images in a grouping state, and a finding selection screen generation unit 68 for generating a selection screen of finding information on which language analysis has been performed.

Figure 3:
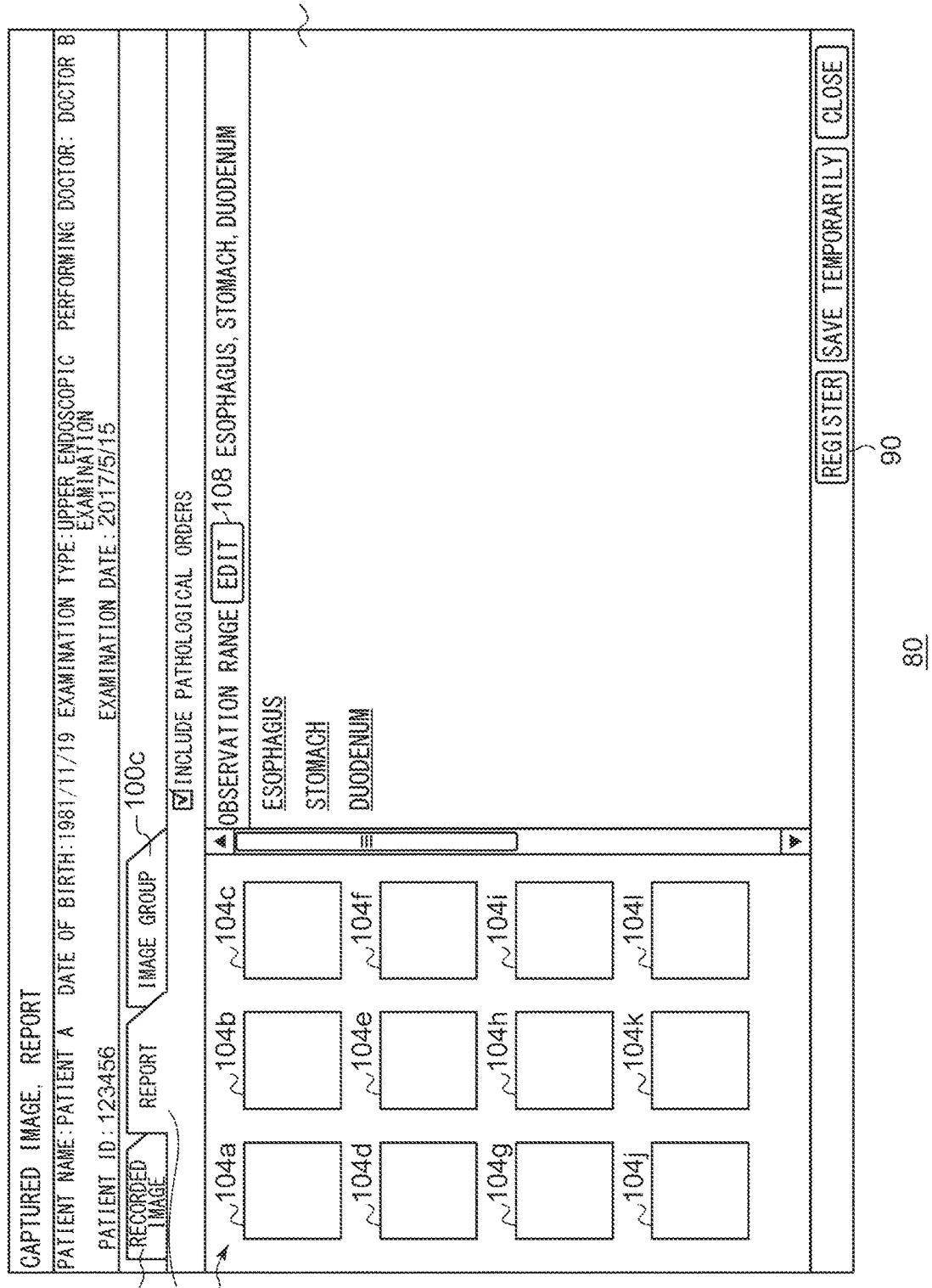
FIG. 3 is a diagram illustrating an example of a report entry screen.

FIG. 3 illustrates an example of a report entry screen. When the display request reception unit 52 receives a report entry screen display request, the report entry screen generation unit 62 generates a report entry screen for a doctor to enter a diagnosis detail and causes the display device 80 to display the report entry screen. During the display of the report entry screen, a report tab 100b is being selected. In the upper part of the report entry screen, information on a patient name, a patient ID, the date of birth, an examination type, an examination date, and a performing doctor obtained from the order information storage 24 are displayed. The report entry screen is composed of two areas. An examination image display area 102 for displaying thumbnails of examination images is provided on the left side, and an examination result entry area 110 for a doctor to enter examination results such as diagnosis details is provided on the right side.

The report entry screen generation unit 62 displays thumbnails 104a to 104l of the examination images acquired by the image acquisition unit 70 from the examination image storage 28 side by side in the examination image display area 102. A scroll bar is provided on the right side of the examination image display area 102, and the doctor can scroll the scroll bar to observe all the thumbnails of the examination images. The doctor selects an examination image to be attached to a report while observing the examination images.

The examination result entry area 110 is an area for a doctor to enter an examination result. In the example shown in the figure, an area is provided for entering diagnosis details for "esophagus", "stomach", and "duodenum" that are observation ranges in an upper endoscopic examination are displayed. When an edit button 108 is operated, selections for an observation range are displayed in a menu window so that the doctor can select an observation range to be diagnosed. The examination result entry area 110 may have a format where a plurality of selections are displayed for examination results such that the doctor enters a diagnosis detail by selecting a check box or may have a free format for free text entry.

In the report entry screen, the doctor selects an examination image to be attached to the report from the examination image display area 102 and enters the examination result including a diagnosis detail in the examination result entry area 110. The diagnosis detail reception unit 54 receives report information including the diagnosis detail entered by the doctor on the report entry screen.

In the medical information processing system 1, information regarding a finding extracted by the voice processing unit 32 is used when entering finding information regarding the image to be attached to the report. As described above, the voice processing unit 32 extracts utterance by the doctor as finding information that can be entered to the report entry screen. In the embodiment, a process of associating the extracted finding information with the examination image is performed. By associating the finding information with the examination image in advance, the associated finding information can be displayed when the examination image is selected.

Referring back to FIG. 1, the grouping processing unit 74 groups a plurality of examination images into one or more image groups based on at least image-capturing time information. FIG. 4 illustrates an example of metadata of an examination image. Image numbers 1 to 21 are the numbers of examination images indicated by thumbnails 104a to 104u, and the image numbers express the order of image capturing. The "image-capturing time" indicates an elapsed time from the examination start time. FIG. 4 shows image-capturing time information and observation mode information as metadata of each examination image.

As described above, the grouping processing unit 74 groups a plurality of examination images into a plurality of image groups based on at least image-capturing time information. One image group preferably includes examination images obtained by capturing the image of the same part or a nearby part. The grouping processing unit 74 groups a plurality of examination images using several grouping conditions.

First, the grouping processing unit 74 is based on the condition that the respective image-capturing times of a plurality of examination images included in one image group are next to each other when grouping. Giving an explanation using image numbers that express the image-capturing order, the grouping processing unit 74 includes a plurality of examination images in one image group on condition that the image numbers are continuous. Hereinafter, this condition is referred to as "order condition". The grouping processing unit 74 may set an image group to which only one examination image belongs.

Further, the grouping processing unit 74 may set a condition that the difference between the image-capturing times of temporally adjacent examination images is a predetermined time or less as a grouping condition. This condition is referred to as "difference condition". When a doctor captured a plurality of images of the same part during an examination, the image-capturing interval is expected to be short. Therefore, if the difference between the image-capturing times of temporally adjacent examination images is within 30 seconds, the grouping processing unit 74 may set the examination images to be in the same group, and if the difference exceeds 30 seconds, the grouping processing unit 74 may set the examination images to be in different groups.

Further, the grouping processing unit 74 may use an observation mode as the grouping condition. As described above, the endoscope 12 according to the embodiment has a special light observation function such as NBI (narrow-band light observation), AFI (fluorescence observation), and IRI (infrared light observation) in addition to the normal light observation function. As illustrated in FIG. 4, the metadata of an examination image includes observation mode information, and the grouping processing unit 74 can identify the observation mode of each examination image. During observation in a special light observation mode, a doctor often observes the periphery of a single lesion carefully, and examination images captured at this time are preferably put together as one image group. Therefore, the grouping processing unit 74 may set examination images captured in the same observation mode as one group. This condition is referred to as "observation mode condition".

The grouping processing unit 74 according to the embodiment may group a plurality of examination images using one or more of the order condition, the difference condition, and the observation mode condition. Further, the grouping processing unit 74 may group a plurality of examination images based on characteristics such as the similarity in the tones of color of the examination images. Hereinafter, an example is shown in which the grouping processing unit 74 performs grouping using the order condition and the observation mode condition.

FIG. 5 illustrates the result of grouping by the grouping processing unit 74. The grouping processing unit 74 groups a plurality of examination images using the order condition and the observation mode condition, thereby grouping examination images with image numbers 1 to 5 to be in an image group 1, examination images with image numbers 6 to 13 to be in an image group 2, and examination images with image numbers 14 to 21 to be in an image group 3. In this example, the grouping processing unit 74 uses two conditions, the order condition and the observation mode condition. However, a more detailed grouping process can be performed by combining other conditions.

Figure 6:
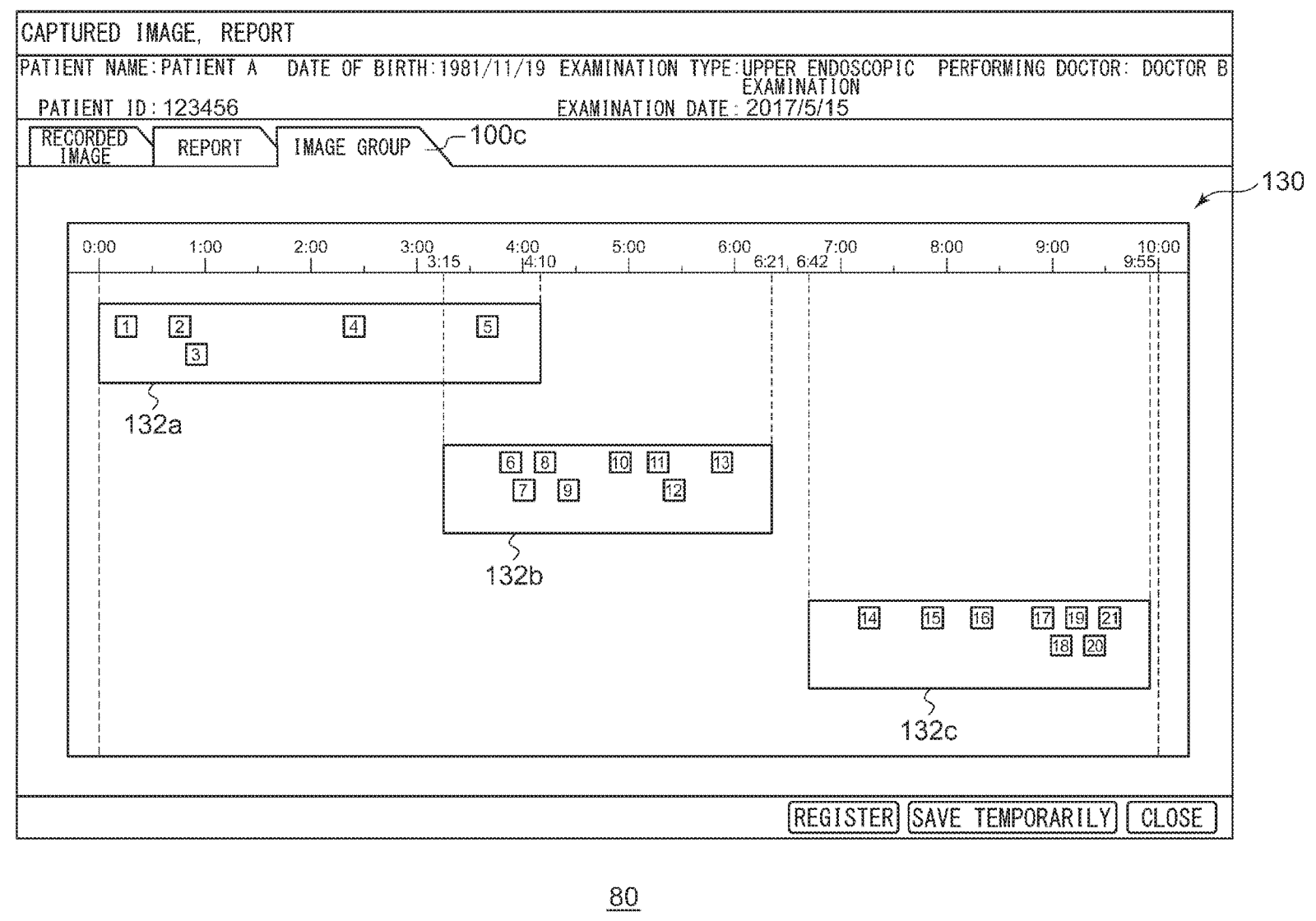

FIG. 6 illustrates an example of a presentation screen for image groups that have been grouped. When a group tab 100c is selected, the group screen generation unit 66 generates an image group presentation screen. In the upper part of the group presentation screen, information on a patient name, a patient ID, the date of birth, an examination type, an examination date, and a performing doctor obtained from the order information storage 24 are displayed. The group screen generation unit 66 displays the result of grouping by the grouping processing unit 74 in a group display area 130. In the group display area 130, a time axis on the horizontal axis indicates the image-capturing time of an examination image. The group screen generation unit 66 expresses the time range of a group using a rectangular group column 132. The group screen generation unit 66 sets the width of the group column 132 by expanding the left end of the group column 132 30 seconds to the left of the image-capturing time of the first image of the group and the right end of the group column 132 30 seconds to the right of the image-capturing time of the last image of the group.

A first group column 132a expresses a group 1 grouped by the grouping processing unit 74. In the first group column 132a, thumbnails with image numbers 1 to 5 are arranged in accordance with the image-capturing time.

A second group column 132b expresses a group 2 grouped by the grouping processing unit 74. In the second group column 132b, thumbnails with image numbers 6 to 13 are arranged in accordance with the image-capturing time.

A third group column 132c expresses a group 3 grouped by the grouping processing unit 74. In the third group column 132c, thumbnails with image numbers 14 to 21 are arranged in accordance with the image-capturing time.

The association processing unit 76 performs a process of associating information regarding a finding stored in the extracted information storage 34 with an image group based on voice time information. When the voice time information associated with the information regarding the finding is included in a time range between a time (initial time) determined by the image-capturing time of the first examination image in the image group and a time (final time) determined by the image-capturing time of the last examination image, the association processing unit 76 associates the information regarding the finding with the image group.

The initial time determined by the image-capturing time of the first examination image in the image group may be the image-capturing time of the first examination image or may be a point of time that is a first predetermined time before the image-capturing time of the first examination image. The final time determined by the image-capturing time of the last examination image in the image group may be the image-capturing time of the last examination image or may be a point of time that is a second predetermined time after the image-capturing time of the last examination image.

As described above, when the voice time information associated with the information regarding the finding is included in the time range between the initial time and the final time, the association processing unit 76 associates the information regarding the finding with the image group. In the medical information processing system 1 according to the embodiment, when a doctor records a finding detail while capturing an internal body image, there are two cases that are expected: a case in which the image capturing is performed after uttering the finding detail first; and a case in which the finding detail is uttered after the image capturing. Therefore, by setting a point of time that is the first predetermined time before the image-capturing time of the first image in the image group as the initial time of the image group and setting a point of time that is the second predetermined time after the image-capturing time of the last image in the image group as the final time of the image group, the information regarding the finding can be effectively associated without omission.

In the embodiment, the first predetermined time is set to 30 seconds, and the second predetermined time is also set to 30 seconds. Therefore, the group screen generation unit 66 sets the width of the group column 132 by expanding the left end of the group column 132 30 seconds to the left of the image-capturing time of the first image of the group and the right end of the group column 132 30 seconds to the right of the image-capturing time of the last image of the group. As a result, the first group column 132a has a time range of 0:00 (examination start time) to 4:10, the second group column 132b has a time range of 3:15 to 6:21, and the third group column 132c has a time range from 6:42 to 9:55.

Figure 7:
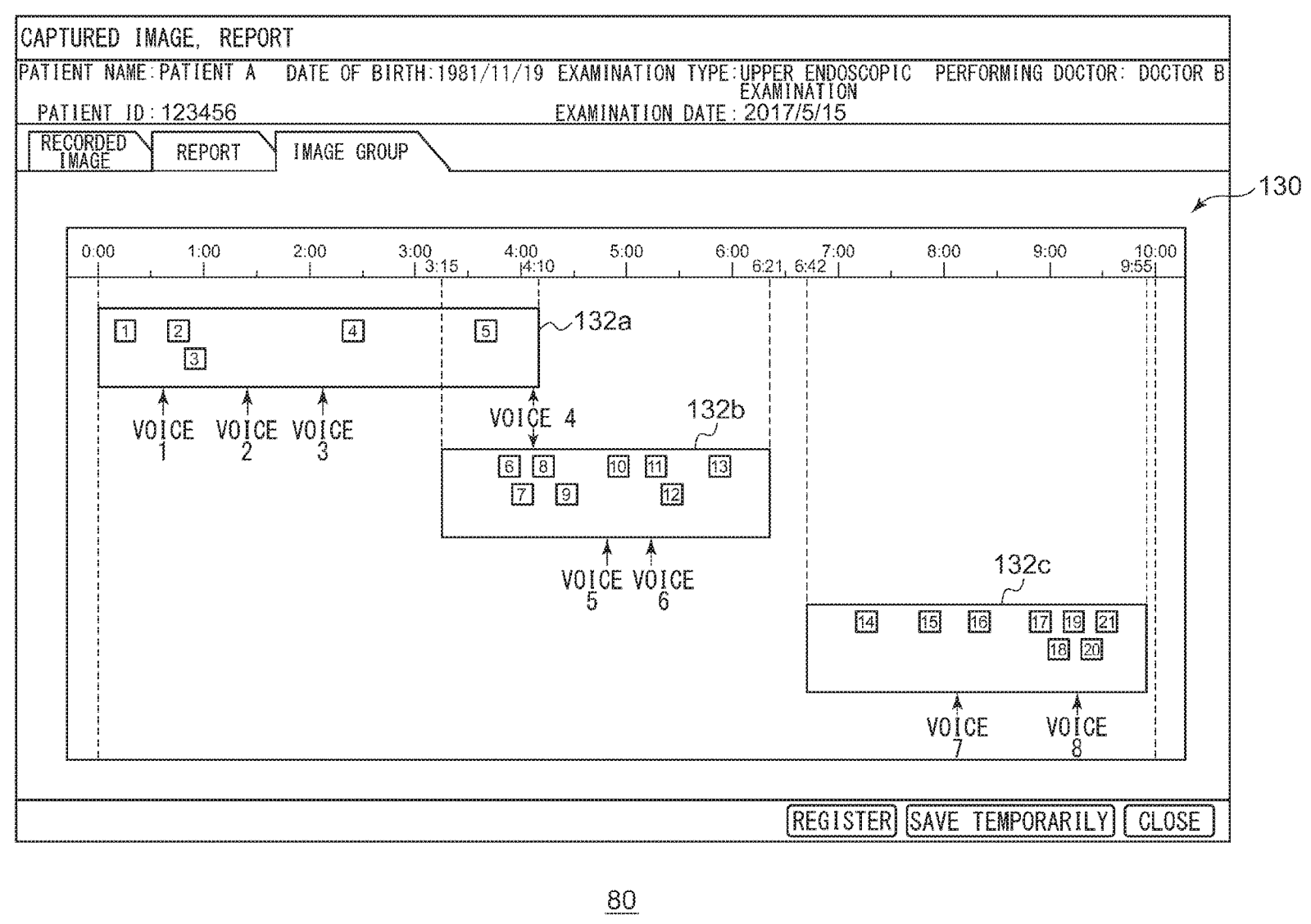

FIG. 7 illustrates the state of association by the association processing unit 76. The voice time shown in FIG. 2 and the image-capturing time shown in FIG. 7 indicate relative times using the examination start time as a reference (0:00). With reference to the voice time information in the extracted information storage 34 shown in FIG. 2, the association processing unit 76 associates extracted findings having the voice data numbers 1 to 4 with the image group 1, associates extracted findings having the voice data numbers 4 to 6 with the image group 2, and associates extracted findings having the voice data numbers 7 to 8 with the image group 3. There is a high possibility that extracted findings associated with an image group based on a voice time are findings uttered by the doctor with regard to the image group. The extracted finding having the voice data number 4 is associated with both the image group 1 and the image group 2. This means that there is a high possibility that this is a finding uttered with regard to at least either one of the groups.

The doctor can change an image group in the group display area 130. For example, the doctor can change the image group by dragging a thumbnail in a group column 132 using a mouse and dropping the thumbnail in another group column 132. When the thumbnail is dropped in an area other than another group column 132, a new group column 132 is generated and displayed. When the image group is changed, the grouping processing unit 74 appropriately changes the group column 132 and displays the group column 132 that has been changed in the group display area 130.

The grouping process by the grouping processing unit 74 and the association process by the association processing unit 76 are performed when the doctor selects an examination for which an examination report is to be prepared from the list of examinations that have already been performed. Therefore, when the report entry screen shown in FIG. 3 is displayed on the display device 80, the association process by the association processing unit 76 has already been completed.

FIG. 8 illustrates an example of a menu window for selecting an image to be attached to a report in a report entry screen. When the doctor selects a thumbnail 104 to be attached to the report in the examination image display area 102 and right-clicks the mouse, a part selection window 112 is displayed.

The part selection window 112 displays an observation range for attaching an image. Three items in the part selection window 112 are items for selecting the observation range for a report attachment image and are, in order from the top, an item for the attachment to the diagnosis result for the observation range "esophagus", an item for the attachment to the diagnosis result for "stomach", and an item for the attachment to the diagnosis result for "duodenum". In this example, the doctor selects a thumbnail 104h and selects "attachment to report (stomach)" in the part selection window 112.

When the doctor selects any of the items using a mouse pointer in the part selection window 112, a detailed part window 114 is displayed in which detailed parts included in the observation range are listed. The detailed part window 114 displays the detailed parts included in the observation range, and the doctor selects any of the detailed parts using the mouse pointer. In this example, as the detailed parts of the stomach, items "his angle", "cardiac region", "angular region", "gastric body", "gastric fundus", "fornix", "pyloric zone", and "pylorus" are set.

Figure 9:
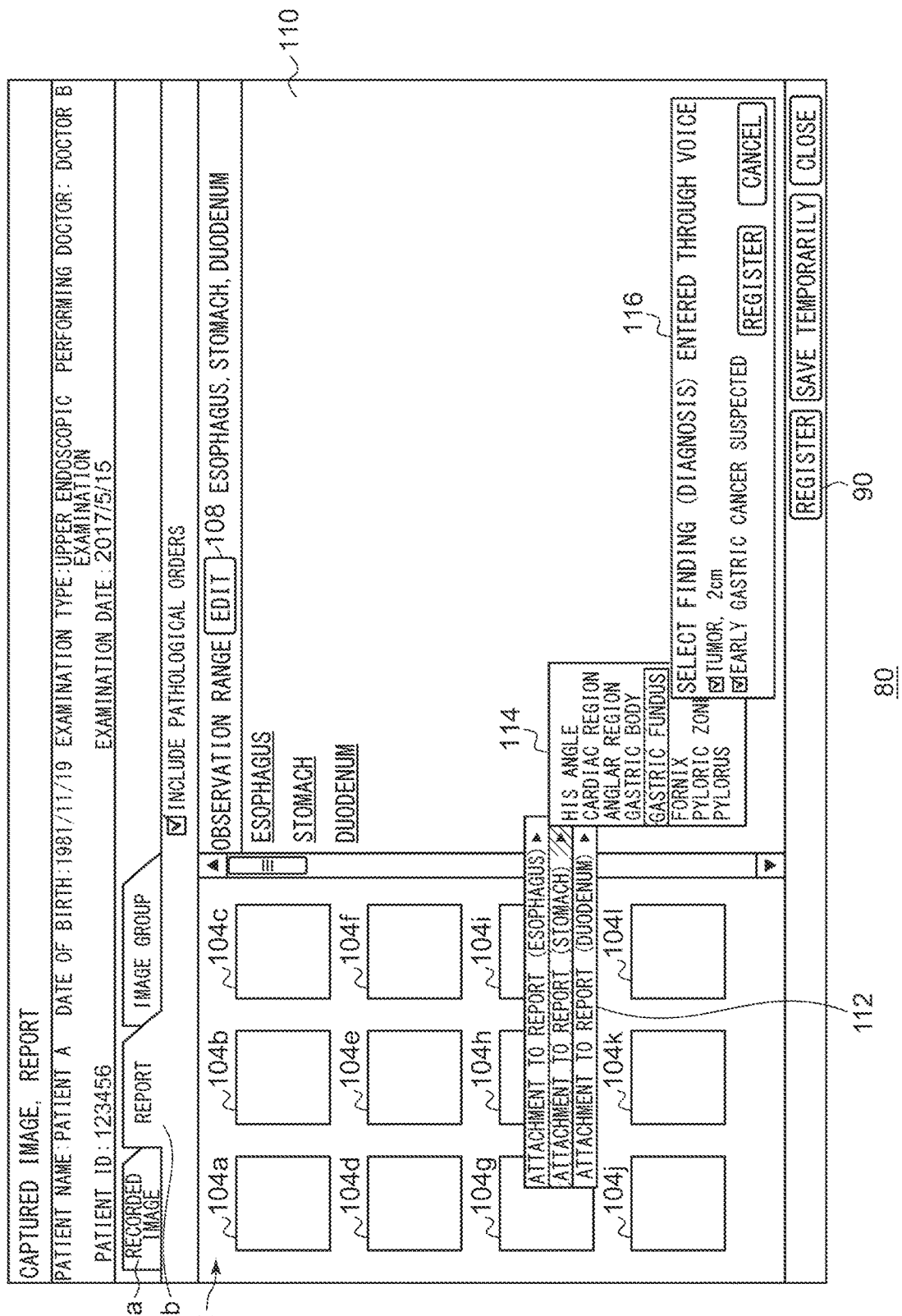
FIG. 9 is a diagram illustrating a state where a detailed part is selected in a detailed part window.

FIG. 9 illustrates a state where a detailed part is selected in the detailed part window 114. The doctor has selected "gastric fundus" in the detailed part window 114. When a detailed part is selected, the observation part of the selected thumbnail 104h is determined, and the finding selection screen generation unit 68 generates a finding selection screen for displaying information regarding a finding associated with an image group including the selected examination image.

The finding selection window 116 is a finding selection screen that displays the information regarding the finding associated with the image group to which the thumbnail 104h belongs in such a manner that the doctor can select the information. Referring to FIG. 5, the thumbnail 104h corresponds to the examination image with the image number 8. In FIG. 7, the examination image with the image number 8 is included in the image group 2, and extracted findings for the voice data numbers 4 to 6 are associated with the image group 2.

As described above, the extracted findings for the voice data numbers 4 and 6 correspond to finding entry items on the report entry screen. However, an extracted finding for the voice data number 5 is not a finding entry item on the report entry screen. Therefore, the finding selection screen generation unit 68 displays the extracted findings for the voice data numbers 4 and 6 on the finding selection window 116 such that the doctor can select the findings. By selecting a check box, the doctor can enter the finding details that are displayed in the finding selection window 116 on the report entry screen.

As shown in FIG. 9, when the user selects a check box for an extracted finding displayed in the finding selection window 116 and presses a registration button inside the finding selection window 116, the diagnosis detail reception unit 54 receives the extracted finding as finding information. This is equivalent to a doctor selecting a finding item from a plurality of selections on the report entry screen.

The finding selection screen generation unit 68 may display an extracted finding for the voice data number 5 on the finding selection window 116 in such a manner that the doctor cannot select the finding. It is true that the doctor has uttered "large" during the examination, and this utterance content has the possibility of affecting the diagnosis. Therefore, displaying "large" in the finding selection window 116 can give the doctor an opportunity to remember the examination status. When there are a plurality of extracted findings that do not correspond to the finding entry items, the finding selection screen generation unit 68 may collectively display the findings on one screen. As described, presenting even an extracted finding that does not correspond to an entry item to the doctor allows the doctor to be given an opportunity to remember the examination status.

Further, the finding selection screen generation unit 68 may display an extracted finding that does not correspond to a finding entry item, in a window in a state where the doctor can select the extracted finding. In this case, even if an extracted finding is selected, the diagnosis detail reception unit 54 does not receive the extracted finding as an finding information entry. However, the report entry screen generation unit 62 may display a plurality of entry items as selections in order for the doctor to be able to enter a finding and may enter an extracted finding that is selected in a free entry field.

The diagnosis detail reception unit 54 receives an operation for selecting an examination image to be attached to an endoscopic examination report and receives finding information entered through the finding selection window 116. The diagnosis detail reception unit 54 stores in the memory 78 that the examination image of the thumbnail 104h is set as an attachment image of the diagnosis result of the stomach, that this image is an image obtained by capturing the image of the "gastric fundus" of the "stomach", that the finding information regarding the gastric fundus of the stomach is "tumor, 2 cm", and that the comprehensive diagnosis is "early gastric cancer suspected". As described above, when a doctor selects an examination image to be attached to a report, finding information entered through voice during the examination can be used for report entry. This reduces the load for input work of the doctor and reduces errors such as missed entry.

In the above, the doctor performs the image selection operation on the report entry screen. Even when a recorded image tab 100a is selected, a list screen of examination images is also displayed on the display device 80, and the doctor can perform the image selection operation.

Figure 10:
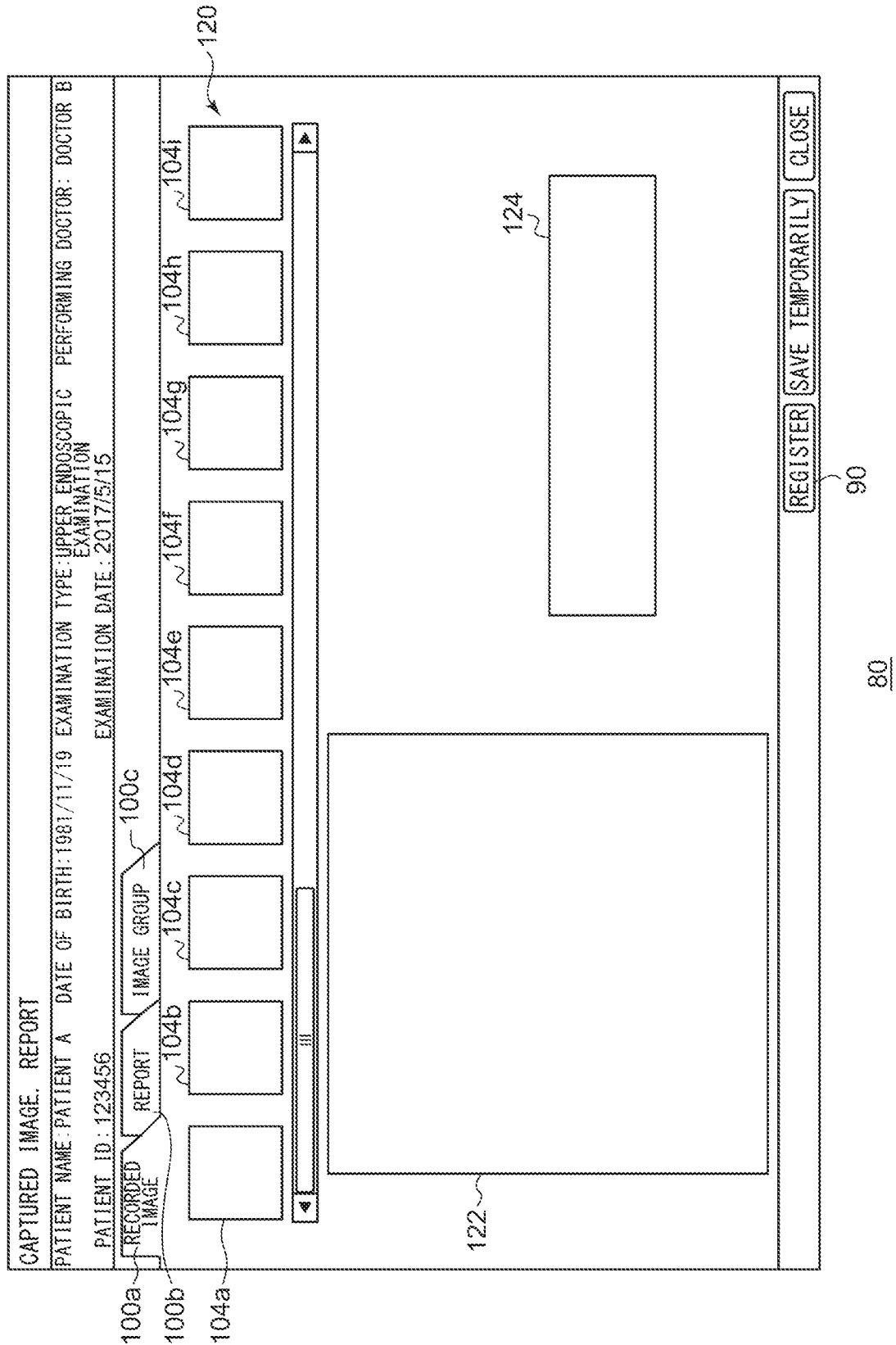
FIG. 10 is a diagram illustrating an example of an examination image selection screen.

FIG. 10 illustrates an example of an examination image selection screen. The selection screen generation unit 64 generates an examination image selection screen. During the display of the selection screen, the recorded image tab 100a is being selected. In the upper part of the selection screen, information on a patient name, a patient ID, the date of birth, an examination type, an examination date, and a performing doctor obtained from the order information storage 24 are displayed. Below the order information, an examination image display area 120 for displaying thumbnails of examination images is provided. The selection screen generation unit 64 displays thumbnails of the examination images acquired by the image acquisition unit 70 from the examination image storage 28 side by side in the examination image display area 120. A scroll bar is provided below the examination image display area 120, and the doctor can scroll the scroll bar to observe all the thumbnails of the examination images.

The doctor can select a report attachment image from either the report entry screen or the selection screen. Also on the selection screen, the part selection window 112, the detailed part window 114, and the finding selection window 116 shown in FIG. 9 are displayed according to the mouse operation by the doctor, and the doctor can register a report attachment image and finding information in the examination result storage 26. An advantage of the selection screen shown in FIG. 10 is that an enlarged display area 122 for displaying the thumbnail 104 in an enlarged manner is provided. When the doctor selects the thumbnail 104 in the examination image display area 120, the thumbnail 104 that is selected is displayed in an enlarged manner in the enlarged display area 122.

The doctor can accurately observe the presence of a lesion from an examination image displayed in an enlarged manner and can effectively determine whether or not to attach the examination image to a report. The doctor can enter a comment regarding the image displayed in an enlarged manner in the enlarged display area 122 in a comment entry field 124. For example, when a display image is reddish, a comment stating "bleeding is confirmed" may be entered in the comment entry field 124. The comment entered in the comment entry field 124 is stored in the memory 78 in association with the image. The comment stored in the memory 78 is later stored in the examination result storage 26 as the examination result along with the diagnosis detail, the report attachment image, etc.

FIG. 11 illustrates examination results including diagnosis details entered on the report entry screen. One or more examination images are attached to each observation range. Examination images of thumbnails 104a and 104c are attached to "esophagus", examination images of thumbnails 104h, 104n, and 104q are attached to "stomach", and an examination image of a thumbnail 104t is attached to "duodenum". The entry area for "stomach" includes finding information and diagnosis information selected in the finding selection window 116. The information entered on the report entry screen is temporarily stored in the memory 78.

When the doctor operates a registration button 90 after entering the examination result, the registration processing unit 72 transmits information stored in the memory 78 to the management system 20. In the memory 78, in addition to a diagnosis result entered on the report entry screen, an examination image selected as a report attachment image, and a comment entered for the examination image, examination information such as the patient name, the patient ID, the date of birth, the examination type, the examination date, and the performing doctor is stored. The registration processing unit 72 instructs the management system 20 to register the diagnosis result, the report attachment image, the additional comment, and the examination information in the examination result storage 26.

In the management system 20, based on an instruction from the registration processing unit 72, the registration unit 22 stores the diagnosis result, the examination result including the report attachment image and the additional comment, and the examination information such as the examination type in the examination result storage 26 as the report information in association with the doctor ID for identifying the doctor who has entered the entry. The report information stored in the examination result storage 26 is printed in a predetermined format and used as an examination report.

Described above is an explanation based on the embodiments of the present invention. These embodiments are intended to be illustrative only, and it will be obvious to those skilled in the art that various modifications to constituting elements and processes could be developed and that such modifications are also within the scope of the present invention.

What is claimed is:
1. A medical information processing system comprising:
a processor comprising hardware; an examination image storage that stores a plurality of examination images having image-capturing time information indicating image-capturing time and observation mode information indicating an observation mode of an endoscope; and an extracted information storage that stores information regarding a finding extracted based on voice that is input to a voice input unit and voice time information indicating the time the voice is input to the voice input unit in association with each other,
wherein the processor is configured to:
group a plurality of examination images into one or more image groups based on the image-capturing time information and the observation mode information, and
associate information regarding the finding stored in the extracted information storage with the image group based on the voice time information.
2. The medical information processing system according to claim 1,
wherein the observation mode of the endoscope includes a normal light observation mode using white light and a special light observation mode using at least one of narrowband light, fluorescence light, and infrared light.
3. The medical information processing system according to claim 1,
wherein the processor is configured to:
associate the information regarding the finding with the image group when the voice time information associated with the information regarding the finding is included in a time range between a time determined by the image-capturing time of the first examination image in the image group and a time determined by the image-capturing time of the last examination image.
4. The medical information processing system according to claim 3,
wherein the time range is a range from a point of time that is a first predetermined period of time before the image-capturing time until a point of time that is a second predetermined time after the image-capturing time of the last examination image.

5. The medical information processing system according to claim 1,
wherein the medical information processing system further comprises a voice storage that stores the voice that is input to the voice input unit during the examination in association with the voice time information, and
wherein the voice stored in the voice storage is recognized after the examination is completed.

6. The medical information processing system according to claim 1,
wherein the processor is configured to:
generate a first screen that displays a plurality of examination images;
generate, when one examination image is selected by a user on the first screen, a second screen that displays information regarding a finding associated with an image group including the examination image that is selected.

7. The medical information processing system according to claim 6,
wherein the processor is configured to:
when the information regarding the finding is selected by the user on the second screen, receive the selection as a finding information entry.

8. The medical information processing system according to claim 1,
wherein the processor is configured to:
group an examination image based on information attached to the examination image.

9. The medical information processing system according to claim 1,
wherein the image group can be changed by a user.

10. The medical information processing system according to claim 1,
wherein the medical information processing system further comprises a buffer that stores the voice that is input to the voice input unit during the examination in association with the voice time information, and
wherein the voice stored in the buffer is recognized in real time.

11. A medical information processing method comprising:
storing a plurality of examination images having image-capturing time information indicating image-capturing time and observation mode information indicating an observation mode of an endoscope;
extracting information regarding a finding based on voice that is input to a voice input unit;
storing information regarding the finding that is extracted and voice time information indicating the time the voice is input to the voice input unit in association with each other;
grouping a plurality of examination images into one or more image groups based on the image-capturing time information and the observation mode information, and
associating information regarding the finding that is stored with the image group based on the voice time information.

* * * * *